(12) United States Patent
Graw

(10) Patent No.: US 7,136,692 B2
(45) Date of Patent: Nov. 14, 2006

(54) INTEGRATED AUDIO VISUAL SYSTEM FOR NUCLEAR MEDICINE IMAGING SYSTEMS

(75) Inventor: Ansgar Graw, Arlington Heights, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 636 days.

(21) Appl. No.: 10/107,214

(22) Filed: Mar. 28, 2002

(65) Prior Publication Data

US 2003/0187346 A1    Oct. 2, 2003

(51) Int. Cl.
*A61B 6/00* (2006.01)
(52) U.S. Cl. .................. 600/436; 250/363.02
(58) Field of Classification Search ............ 600/407, 600/410, 431, 436, 418; 345/8; 250/363.02–363.08
See application file for complete search history.

(56) References Cited

U.S. PATENT DOCUMENTS

| | | | |
|---|---|---|---|
| 4,939,464 A * | 7/1990 | Hammer | 600/436 |
| 5,339,813 A * | 8/1994 | DeYoe et al. | |
| 5,733,247 A * | 3/1998 | Fallon | 600/410 |
| 5,800,355 A * | 9/1998 | Hasegawa | 600/436 |
| 5,861,865 A * | 1/1999 | Anand et al. | 345/126 |
| 5,877,732 A * | 3/1999 | Ziarati | 345/8 |
| 6,219,570 B1 * | 4/2001 | Mueller et al. | 600/410 |
| 6,373,060 B1 * | 4/2002 | Yamakawa et al. | 250/363.08 |
| 6,490,476 B1 * | 12/2002 | Townsend et al. | 600/427 |

* cited by examiner

*Primary Examiner*—Ruth S. Smith

(57) ABSTRACT

A nuclear medicine imaging system including a gantry disposed above a table with a photo detector mounted on the gantry for performing imaging. The table may be fixed beneath the gantry or movable. A video screen is mounted on the gantry or on the table, along with an audio speaker, so as to remain substantially motionless relative to the table. The table may include an aperture through which the video screen may be viewed. A media player is connected communicably to the video screen by a first channel and to the audio speaker by a second channel, so that a patient on the table may view the video screen and listen to the audio speaker while undergoing imaging.

16 Claims, 4 Drawing Sheets

INTEGRATED AUDIO VISUAL SYSTEM FOR NUCLEAR MEDICINE IMAGING SYSTEMS

BACKGROUND OF THE INVENTION

1. Field of the Invention

The present invention relates generally to nuclear medicine, and to systems for obtaining nuclear medicine images of a patient's body organs of interest. In particular, the present invention relates to systems and methods for diverting the attention of a patient while obtaining nuclear medicine images of the patient's organs of interest.

2. Description of the Background Art

Nuclear medicine is a unique medical specialty wherein radiation is used to acquire images that show the function and anatomy of organs, bones or tissues of the body. Radiopharmaceuticals are introduced into the body, either by injection or ingestion, and are attracted to specific organs, bones or tissues of interest. Such radiopharmaceuticals produce gamma photon emissions that emanate from the body and are captured by a scintillation crystal, with which the photons interact to produce flashes of light or "events."

Events are detected by an array of photodetectors, such as photo multiplier tubes, and their spatial locations or positions are calculated and stored. In this way, an image of the organ or tissue under study is created from detection of the distribution of the radioisotopes in the body.

It is very important for a patient who is undergoing such imaging to remain as motionless as possible. Movement by the patient during imaging produces spurious artifacts in the images. It may be difficult for a patient to remain motionless during the imaging process, however, since the imaging process may go on for some time.

A patient may also be nervous and apprehensive about the procedure. Indeed, visiting a hospital may well induce fear that borders on paranoia in some patients. Feelings of helplessness, such as may be associated with being strapped to a table moving through a large machine, can incite a flight reflex in a patient. Since patients who are struggling to control their flight reflex may exhibit an inability to keep still, this may also be detrimental to the imaging process.

It would be desirable for a patient who is undergoing imaging to have something else to think about. Having a video to view while the imaging is taking place may take the patient's mind off of the procedure, and enable them to remain still. Commonly available home entertainment systems, such as stereos and televisions, are not generally adapted to a hospital environment. Hospital equipment may be subject to rigorous standards for, e.g. cleanliness, fire prevention, and explosion proofing that commonly available entertainment systems may not meet.

Furthermore, a patient who is undergoing imaging may be placed in a position that is convenient for a photo detector, but inconvenient for comfortable viewing of, e.g. a video screen. It would therefore be desirable for a video screen to be adjustable to suit a particular position or orientation of a patient undergoing imaging.

Finally, a patient may be moved through a imaging system during the procedure. It would be desirable for the patient to be able to view continuously a video screen without having to turn his head or adjust his position during the imaging process.

Thus, there remains a need in the art to improve upon diverting the attention of a patient while obtaining nuclear medicine images of the patient's organs of interest.

SUMMARY OF THE INVENTION

The present invention solves the existing need by providing in a first embodiment a nuclear medicine imaging system including a gantry disposed above a table with a photo detector mounted on the gantry for performing imaging. A video screen is mounted on the gantry substantially normal to the table, along with an audio speaker, and a media player is connected communicably to the video screen by a first channel and to the audio speaker by a second channel, so that a patient may view the video screen and listen to the audio speaker while undergoing imaging.

The invention provides in a second embodiment a nuclear medicine imaging system including a gantry and a table disposed movably beneath the gantry. A photo detector is mounted on the gantry for performing imaging. A video screen is mounted on the table substantially normal to the table along with an audio speaker, and a media player is connected communicably to the video screen by a first channel and to the audio speaker by a second channel, so that a patient may view the video screen and listen to the audio speaker while undergoing imaging.

The invention provides in a third embodiment a nuclear medicine imaging system including a gantry disposed above a table having an aperture, with a photo detector mounted on the gantry for performing imaging. A video screen is disposed beneath the aperture substantially normal to the table, along with an audio speaker, and a media player is connected communicably to the video screen by a first channel and to the audio speaker by a second channel, so that a patient may view the video screen through the aperture and listen to the audio speaker while undergoing imaging.

DETAILED DESCRIPTION OF THE PREFERRED EMBODIMENTS

Figure 1:
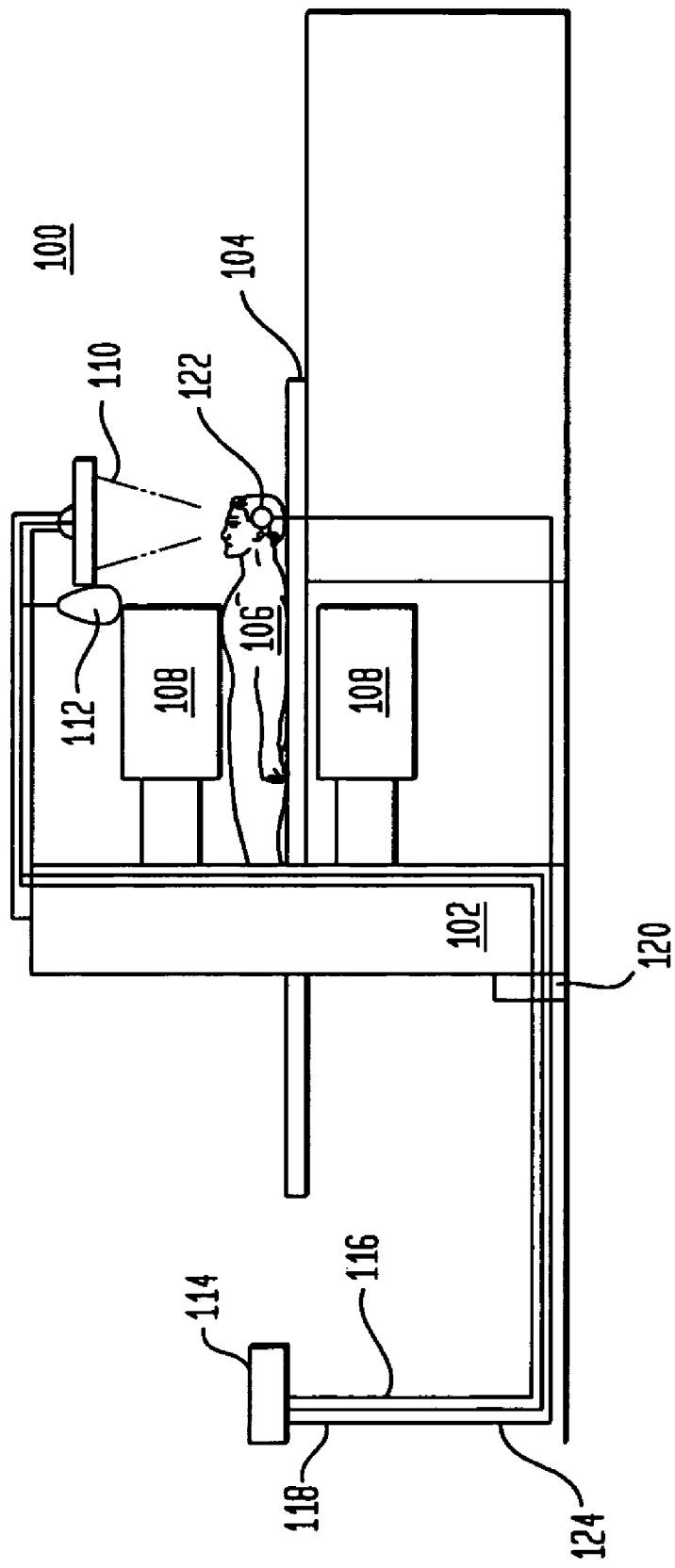
FIG. 1 is a side view of a nuclear medicine imaging system according to a first embodiment of the invention.

In FIG. 1 is shown a nuclear medicine imaging system 100 according to a first embodiment of the invention. All references to, e.g. 'his' in the following description should be read as 'his or her'. System 100 may include, e.g., a gantry 102 disposed above a table 104 upon which a patient 106 may be placed while undergoing imaging.

The patient 106 may be placed in a variety of positions or orientations during imaging, depending on the particular needs of the imaging process. Patient 106 may be placed, e.g. on his back, his stomach, his left or right side, or in a position intermediate between a pair of these by providing appropriate supports.

A photo detector 108 may be mounted on gantry 102 for performing imaging. A video screen 110 may be mounted on gantry 102 substantially normal to table 104, along with an audio speaker 112. Video screen 110 may be integrated with audio speaker 112. Video screen 110 may be, e.g. two or more video screens, such as may be used for, e.g. a presentation in three dimensions, such as for a 3-D display. Video screen 110 may also be, e.g. a flat panel display, a cathode ray tube (CRT), a holographic display, a projection system, a liquid crystal display (LCD), or a light emitting diode (LED) display. Audio speaker 112 may also be, e.g. two or more audio speakers, such as might be used with stereo, theater, or surround sound.

A media player 114 may be connected communicably to video screen 110 by a first channel 116 and to audio speaker 112 by a second channel 118. Media player 114 may be, e.g. a digital video disk (DVD) player, a compact disk (CD) player, a video cassette recorder (VCR), a video player, or a television. First channel 116 may be, e.g. a radio frequency (RF) signal, a coaxial cable, a twisted pair, or an optical fiber. Second channel 118 may be, e.g. a RF signal, a coaxial cable, a twisted pair, or an optical fiber.

In a preferred embodiment, video screen 110 may be adjustable so patient 106 may view video screen 110 while undergoing imaging, regardless of the particular position or orientation of patient 106 on table 104. Audio speaker 112 may also be adjustable so patient 106 may experience the full effect of audio speaker 112 while undergoing imaging, regardless of the particular position or orientation of patient 106 on table 104. Patient 106 may thus view video screen 110 and listen to audio speaker 112 while undergoing imaging.

In one embodiment, first channel 116 includes a standard interface 120 interposed between media player 114 and video screen 110. This would allow, e.g. a media player 114 to be plugged in to an existing system 100. This would liberate a user of system 100 to be able to change the form of media player 114, if, e.g. a newer technology or format becomes available. In a preferred embodiment, standard interface 120 may be mounted on gantry 102.

In another embodiment, second channel 118 may also include a standard interface 120 interposed between media player 114 and audio speaker 112. Although a single standard interface 120 is shown in FIG. 1, a separate standard interface 120 may be provided for each of first and second channels 116 and 118, as would be known in the art.

In a further embodiment, a headphone 122 may be connected communicably to media player 114 by a third channel 124. Third channel 124 may be, e.g. a RF signal, a coaxial cable, a twisted pair, or an optical fiber.

Figure 2:
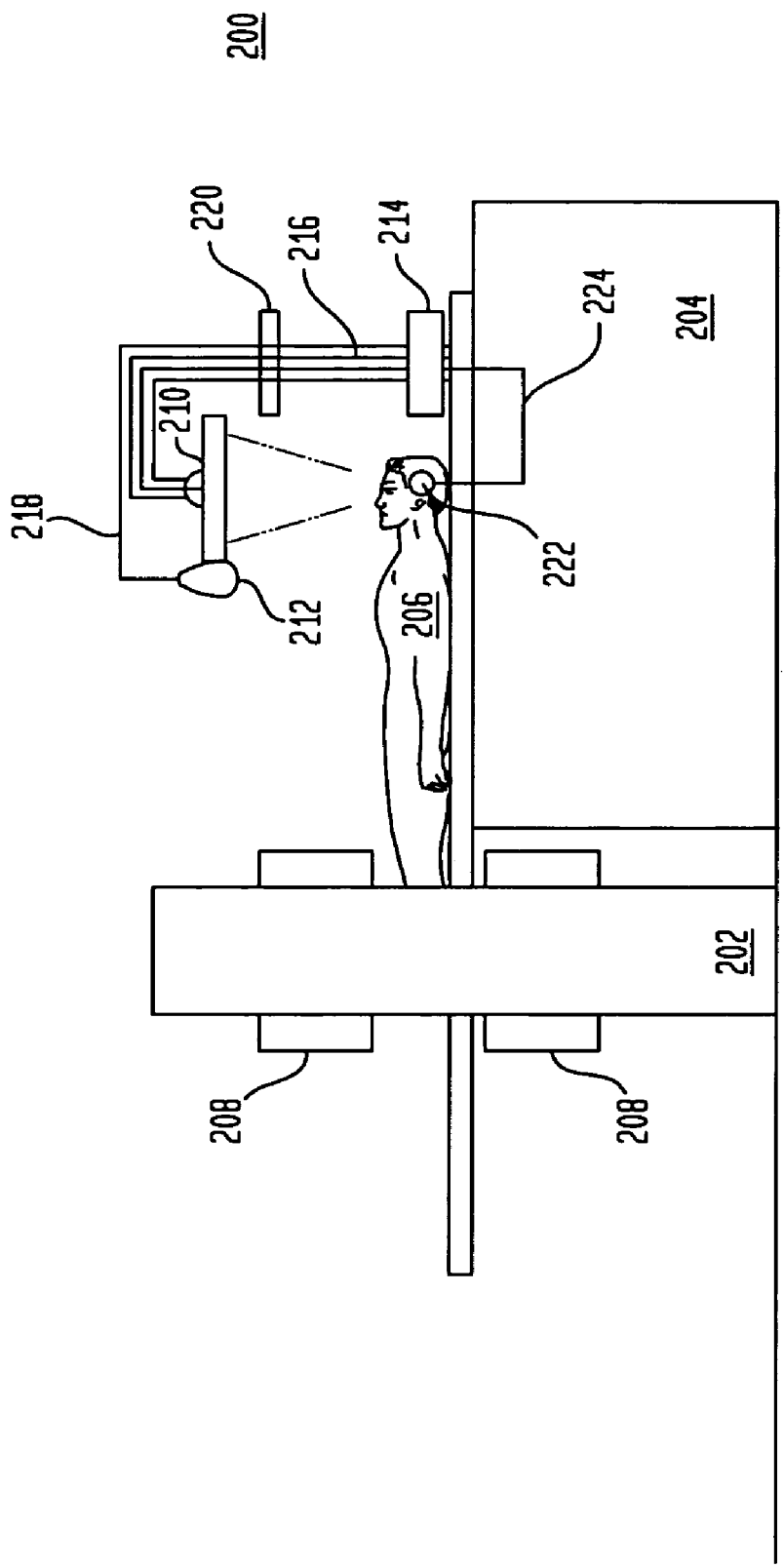
FIG. 2 is a side view of a nuclear medicine imaging system according to a second embodiment of the invention.

In FIG. 2 is shown a nuclear medicine imaging system 200 according to a second embodiment of the invention. System 200 may include, e.g. a gantry 202 and a table 204 disposed movably beneath gantry 202, upon which a patient 206 may be placed while undergoing imaging. Table 204 may be moved beneath gantry 202 during the imaging process if e.g. a succession of images is to be taken of patient's 206 body. This may be the case during, e.g. a whole-body imaging of patient 206.

The patient 206 may be placed in a variety of positions or orientations during imaging, depending on the particular needs of the imaging process. Patient 206 may be placed, e.g. on his back, his stomach, his left or right side, or in a position intermediate between a pair of these by providing appropriate supports.

A photo detector 208 may be mounted on gantry 202 for performing imaging. A video screen 210 may be mounted on table 204 substantially normal to table 204, along with an audio speaker 212, so they move along with table 204. Video screen 210 may be integrated with audio speaker 212. The field of view of video screen 210 will thus not shift substantially relative to patient 206 while patient 206 is undergoing imaging. Patient 206 may thus view video screen 210 and listen to audio speaker 212 while undergoing imaging.

Video screen 210 may be, e.g. two or more video screens, such as may be used for, e.g. a presentation in three dimensions, such as for a 3-D display. Video screen 210 may also be, e.g. a flat panel display, a CRT, a holographic display, a projection system, a liquid crystal display, or an LED display. Audio speaker 212 may also be, e.g. two or more audio speakers, such as might be used with stereo, theater, or surround sound.

A media player 214 may be connected communicably to video screen 210 by a first channel 216 and to audio speaker 212 by a second channel 218. Media player 214 may be, e.g. a DVD player, a CD player, a VCR, a video player, or a television. First channel 216 may be, e.g. a RF signal, a coaxial cable, a twisted pair, or an optical fiber. Second channel 218 may be, e.g. a RF signal, a coaxial cable, a twisted pair, or an optical fiber.

In a preferred embodiment, video screen 210 may be adjustable so patient 206 may view video screen 210 while undergoing imaging, regardless of the particular position or orientation of patient 206 on table 204. Audio speaker 212 may also be adjustable so patient 206 may experience the full effect of audio speaker 212 while undergoing imaging, regardless of the particular position or orientation of patient 206 on table 204.

In one embodiment, first channel 216 includes a standard interface 220 interposed between media player 214 and video screen 210. This would allow, e.g. a media player 214 to be plugged in to an existing system 200. This would liberate a user of system 200 from having to stick with a particular form of media player 214, if, e.g. a newer technology or format becomes available. In a preferred embodiment, standard interface 220 may be mounted on table 204.

In another embodiment, second channel 218 may also include a standard interface 220 interposed between media player 214 and audio speaker 212. Although a single standard interface 220 is shown in FIG. 2, a separate standard interface 220 may be provided for each of first and second channels 216 and 218, as would be known in the art.

In a further embodiment, a headphone 222 may be connected communicably to media player 214 by a third channel 224. Third channel 224 may be, e.g. a RF signal, a coaxial cable, a twisted pair, or an optical fiber.

Figure 3:
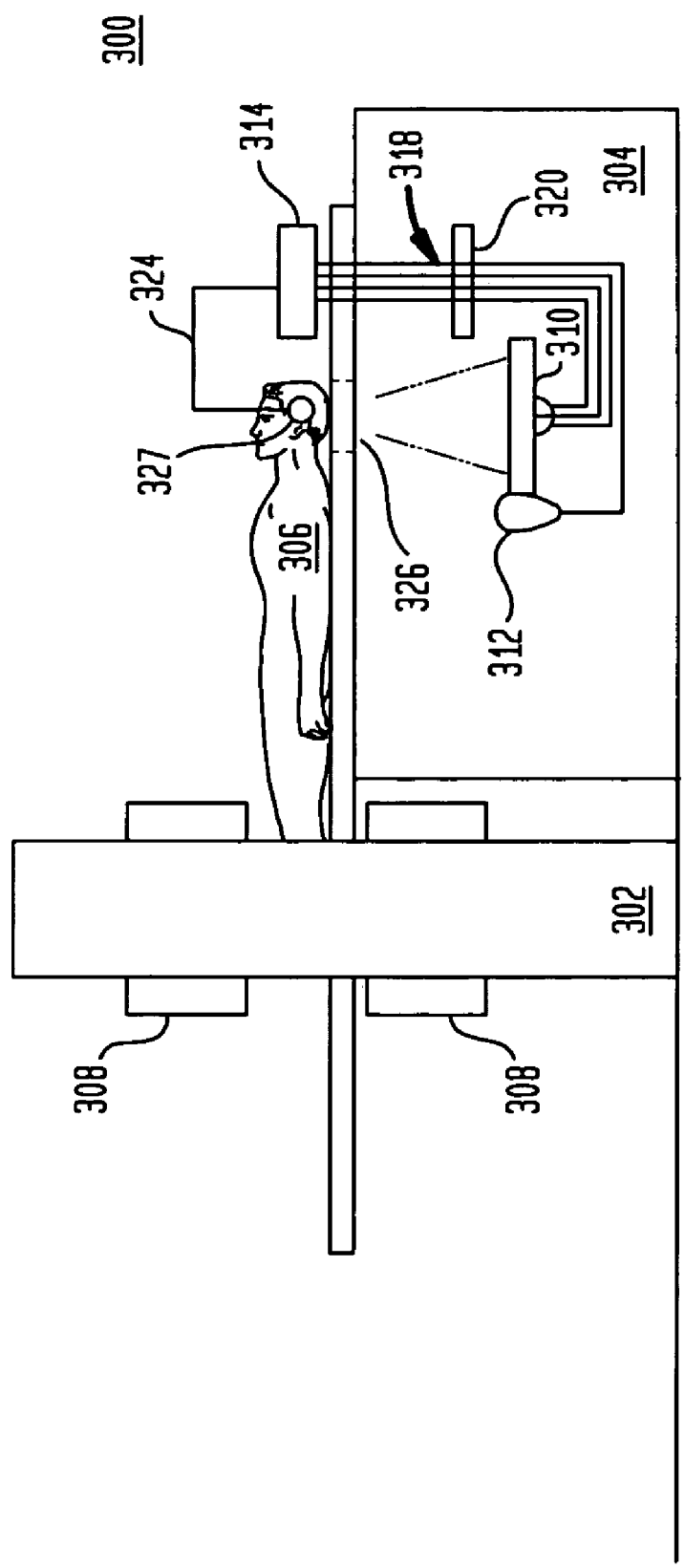
FIG. 3 is a side view of a nuclear medicine imaging system according to a third embodiment of the invention.

In FIG. 3 is shown a nuclear medicine imaging system 300 according to a third embodiment of the invention. System 300 may include, e.g., a gantry 302 disposed above a table 304 upon which a patient 306 may be placed while undergoing imaging. Table 304 may further include an aperture 326 over which patient 306 may place his face while undergoing imaging in, e.g. a facedown position. Aperture 326 may be adapted to fit a range of standard face sizes by providing, e.g. an adaptable collar or rim of a pliable material.

A photo detector 308 may be mounted on gantry 302 for performing imaging. A video screen 310 may be mounted beneath aperture 326 substantially normal to table 304, along with an audio speaker 312. Video screen 310 may be integrated with audio speaker 312. The field of view of video screen 310 will thus be substantially accessible to patient 306 while patient 306 is undergoing imaging. Patient 306 may thus view video screen 310 through aperture 326 and listen to audio speaker 312 while undergoing imaging.

Video screen 310 may be, e.g. two or more video screens, such as may be used for, e.g. a presentation in three dimensions, such as for a 3-D display. Video screen 310 may also be, e.g. a flat panel display, a CRT, a holographic display, a projection system, a liquid crystal display, or an LED display. Audio speaker 312 may also be, e.g. two or more audio speakers, such as might be used with stereo, theater, or surround sound.

A media player 314 may be connected communicably to video screen 310 by a first channel 316 and to audio speaker 312 by a second channel 318. Media player 314 may be, e.g. a DVD player, a CD player, a VCR, a video player, or a television. First channel 316 may be, e.g. a RF signal, a coaxial cable, a twisted pair, or an optical fiber. Second channel 318 may be, e.g. a RF signal, a coaxial cable, a twisted pair, or an optical fiber.

In a preferred embodiment, video screen 310 may be adjustable so patient 306 may view video screen 310 while undergoing imaging, regardless of the particular position or orientation of patient 306 on table 304. Audio speaker 312 may also be adjustable so patient 306 may experience the full effect of audio speaker 312 while undergoing imaging, regardless of the particular position or orientation of patient 306 on table 304.

In one embodiment, first channel 316 includes a standard interface 320 interposed between media player 314 and video screen 310. This would allow, e.g. a media player 314 to be plugged in to an existing system 300. This would liberate a user of system 300 from having to stick with a particular form of media player 314, if, e.g. a newer technology or format becomes available. In a preferred embodiment, standard interface 320 may be mounted on table 304.

In another embodiment, second channel 318 may also include a standard interface 320 interposed between media player 314 and audio speaker 312. Although a single standard interface 320 is shown in FIG. 3, a separate standard interface 320 may be provided for each of first and second channels 316 and 318, as would be known in the art.

In a further embodiment, a headphone 322 may be connected communicably to media player 314 by a third channel 324. Third channel 324 may be, e.g. a RF signal, a coaxial cable, a twisted pair, or an optical fiber.

Figure 4:
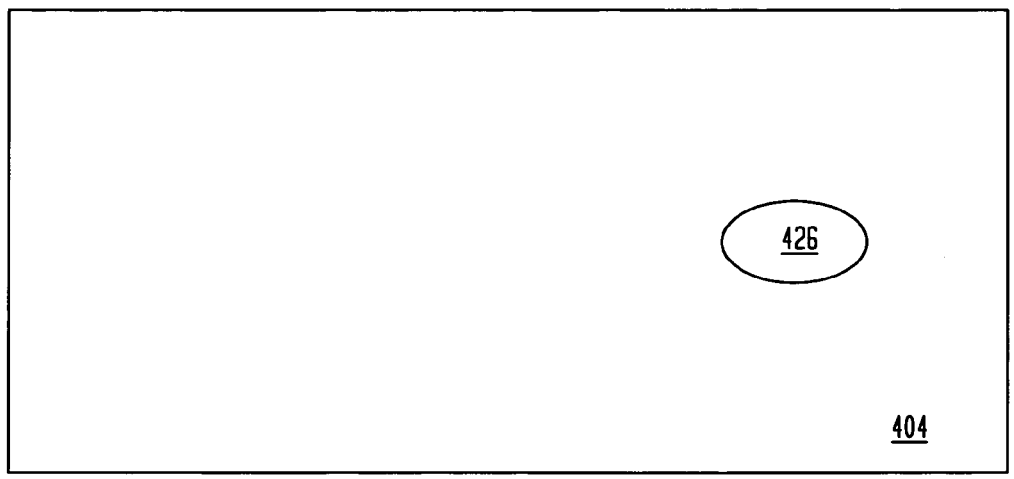
FIG. 4 is a top view of the table of the embodiment shown in FIG. 3.

In FIG. 4 is shown a table 404 with an aperture 426 for use with the third embodiment.

While the invention has been described in detail above, the invention is not intended to be limited to the specific embodiments as described. It is evident that those skilled in the art may now make numerous uses and modifications of and departures from the specific embodiments described herein without departing from the inventive concepts.

What is claimed is:

1. A nuclear medicine imaging system comprising:
   a table;
   a gantry disposed above said table;
   a photo detector mounted on said gantry for performing imaging of a radiation field emanating from a patient lying on said table;
   a video screen mounted within said system so that it can be viewed by said patient;
   an audio speaker provided with said system such that sound emanating therefrom may be heard by said patient;
   a media player connected communicably to said video screen by a first channel and to said audio speaker by a second channel;
   wherein said first channel comprises further a standard interface mounted on said gantry and interposed between said media player and said video screen; and
   wherein a patient may view said video screen and listen to sound from said audio speaker while undergoing said imaging.

2. The nuclear medicine imaging system of claim 1, wherein an orientation of said video screen is adjustable to adapt to a patient's field of view.

3. The nuclear medicine imaging system of claim 1, wherein said second channel comprises further a standard interface interposed between said media player and said audio speaker.

4. The nuclear medicine imaging system of claim 3, wherein said standard interface of said second channel is mounted on said gantry.

5. The nuclear medicine imaging system of claim 1, wherein said first channel is selected from the group consisting of:
   a RF signal,
   a coaxial cable,
   a twisted pair, and
   an optical fiber.

6. The nuclear medicine imaging system of claim 1, wherein said second channel is selected from the group consisting of:
   a RF signal,
   a coaxial cable,
   a twisted pair, and
   an optical fiber.

7. The nuclear medicine imaging system of claim 1, wherein said audio speaker comprises a headphone connected communicably to said media player.

8. The nuclear medicine imaging system of claim 7, wherein said headphone is connected to said media player by a third channel, wherein said third channel is selected from the group consisting of:
   a RF signal
   a coaxial cable,
   a twisted pair, and
   an optical fiber.

9. The nuclear medicine imaging system of claim 1, wherein said media player is selected from the group consisting of:
   a DVD player,
   a CD player,
   a VCR,
   a video player, and
   a television.

10. The nuclear medicine imaging system of claim 1, wherein said video screen is selected from the group consisting of:
    a flat panel display,
    a CRT,
    a holographic display,
    a 3-D display,
    a projection system,
    a liquid crystal display, and
    an LED display.

11. A nuclear medicine imaging system, comprising:
    a table;
    a gantry disposed above said table;
    a photo detector mounted on said gantry for performing imaging of a radiation field emanating from a patient lying on said table;
    a video screen mounted within said system so that it can be viewed by said patient;
    an audio speaker provided with said system such that sound emanating therefrom may be heard by said patient;

a media player connected communicably to said video screen by a first channel and to said audio speaker by a second channel;

wherein a patient may view said video screen and listen to sound from said audio speaker while undergoing said imaging, and wherein said video screen is mounted on said table substantially normal to said table.

12. The nuclear medicine imaging system of claim 11, wherein said table has an aperture therein; and wherein said video screen is disposed beneath said aperture substantially normal to said table.

13. The nuclear medicine imaging system of claim 12, wherein said audio speaker is disposed beneath said aperture.

14. The nuclear medicine imaging system of claim 11, wherein said audio speaker is mounted on said table.

15. A nuclear medicine imaging system, comprising:
a table;
a gantry disposed above said table;
a photo detector mounted on said gantry for performing imaging of a radiation field emanating from a patient lying on said table;

a video screen mounted within said system so that it can be viewed by said patient;

an audio speaker provided with said system such that sound emanating therefrom may be heard by said patient;

a media player connected communicably to said video screen by a first channel and to said audio speaker by a second channel; wherein a patient may view said video screen and listen to sound from said audio speaker while undergoing said imaging, and wherein said video screen is mounted on said gantry.

16. The nuclear medicine imaging system of claim 15, wherein said audio speaker is mounted on said gantry.

* * * * *